United States Patent
Gibbons et al.

(10) Patent No.: US 12,029,660 B2
(45) Date of Patent: Jul. 9, 2024

(54) FEMORAL IMPLANT

(71) Applicant: Howmedica Osteonics Corp., Mahwah, NJ (US)

(72) Inventors: Rachel Gibbons, Easton, PA (US); Tatyana Kaverina, Mahwah, NJ (US); Arlen Dale Hanssen, Rochester, MN (US)

(73) Assignee: Howmedica Osteonics Corp., Mahwah, NJ (US)

( * ) Notice: Subject to any disclaimer, the term of this patent is extended or adjusted under 35 U.S.C. 154(b) by 75 days.

(21) Appl. No.: 17/154,662

(22) Filed: Jan. 21, 2021

(65) Prior Publication Data

US 2021/0220150 A1    Jul. 22, 2021

Related U.S. Application Data

(60) Provisional application No. 62/964,330, filed on Jan. 22, 2020.

(51) Int. Cl.
*A61F 2/46* (2006.01)
*A61F 2/30* (2006.01)
*A61F 2/36* (2006.01)

(52) U.S. Cl.
CPC ........ *A61F 2/4607* (2013.01); *A61F 2/30771* (2013.01); *A61F 2/3603* (2013.01);
(Continued)

(58) Field of Classification Search
CPC .. A61F 2/4607; A61F 2/30771; A61F 2/3603; A61F 2002/30062;
(Continued)

(56) References Cited

U.S. PATENT DOCUMENTS 4,990,161 A * 2/1991 Kampner ............ A61F 2/30767
  623/23.34
5,306,311 A * 4/1994 Stone ........................ C08L 1/00
  623/14.12

(Continued)

FOREIGN PATENT DOCUMENTS

| EP | 1297794 A2 | 4/2003 |
| WO | 9317639 A1 | 9/1993 |
| WO | 2009055952 A1 | 5/2009 |

OTHER PUBLICATIONS

Extended European Search Report including Written Opinion for EP21153004.3 dated Jun. 9, 2021; 9 pages.

(Continued)

*Primary Examiner* — Brian A Dukert
*Assistant Examiner* — Melissa A Hoban
(74) *Attorney, Agent, or Firm* — Lerner David LLP

(57) ABSTRACT

A method comprising cutting a channel through a femoral neck and into a femoral head of a femur, and inserting a femoral implant within the channel such that a porous portion of the femoral implant is positioned within the femoral head and a resorbable portion of the femoral implant is positioned within the femoral neck, the porous portion being coupled to the resorbable portion and extending therefrom along a longitudinal axis of the femoral implant, the resorbable portion having a cross-sectional area defined in a plane extending transverse to a longitudinal axis of the femoral implant, the cross-sectional area of the resorbable portion consisting essentially of a resorbable material.

4 Claims, 3 Drawing Sheets

(52) U.S. Cl.
CPC ............... *A61F 2002/30062* (2013.01); *A61F 2002/30224* (2013.01); *A61F 2002/30405* (2013.01); *A61F 2002/30408* (2013.01); *A61F 2002/3085* (2013.01); *A61F 2002/3092* (2013.01); *A61F 2002/3093* (2013.01)

(58) Field of Classification Search
CPC .. A61F 2002/30224; A61F 2002/30405; A61F 2002/30408; A61F 2002/3085; A61F 2002/3092; A61F 2002/3093; A61B 17/8685; A61B 17/742
See application file for complete search history.

(56) References Cited

U.S. PATENT DOCUMENTS

| | | | |
|---|---|---|---|
| 5,755,809 A | 5/1998 | Cohen et al. | |
| 6,471,707 B1 | 10/2002 | Miller et al. | |
| 6,676,704 B1 * | 1/2004 | Pope | A61F 2/40 623/18.11 |
| 8,470,049 B2 * | 6/2013 | Walter | A61F 2/3662 623/23.35 |
| 8,556,972 B2 | 10/2013 | Gordon et al. | |
| 8,579,947 B2 | 11/2013 | Wu | |
| 8,790,402 B2 | 7/2014 | Monaghan et al. | |
| 9,370,427 B2 | 6/2016 | Sidebotham | |
| 2002/0032488 A1 * | 3/2002 | Brekke | A61L 27/38 623/23.72 |
| 2002/0143335 A1 * | 10/2002 | von Hoffmann | A61B 17/8625 606/67 |
| 2003/0083662 A1 * | 5/2003 | Middleton | A61B 17/7098 606/92 |
| 2004/0193156 A1 * | 9/2004 | Waisman | A61B 17/742 606/60 |
| 2005/0112397 A1 * | 5/2005 | Rolfe | A61F 2/4455 606/76 |
| 2005/0169956 A1 * | 8/2005 | Erbe | A61L 27/58 424/602 |
| 2006/0149362 A1 * | 7/2006 | Pedrozo | A61B 17/742 623/1.35 |
| 2008/0249580 A1 | 10/2008 | Evans et al. | |
| 2009/0043397 A1 * | 2/2009 | Park | A61F 2/3662 623/23.11 |
| 2014/0058524 A1 * | 2/2014 | Gray | A61F 2/4261 623/20.17 |
| 2018/0043062 A1 | 2/2018 | Yang et al. | |
| 2019/0105162 A1 * | 4/2019 | Zhang | A61F 2/3662 |

OTHER PUBLICATIONS

Zimmer, Trabecular Metal Osteonecrosis Intervention Implant—Surgical Technique, 2005, pp. 1-4, Zimmer Inc., USA.

* cited by examiner

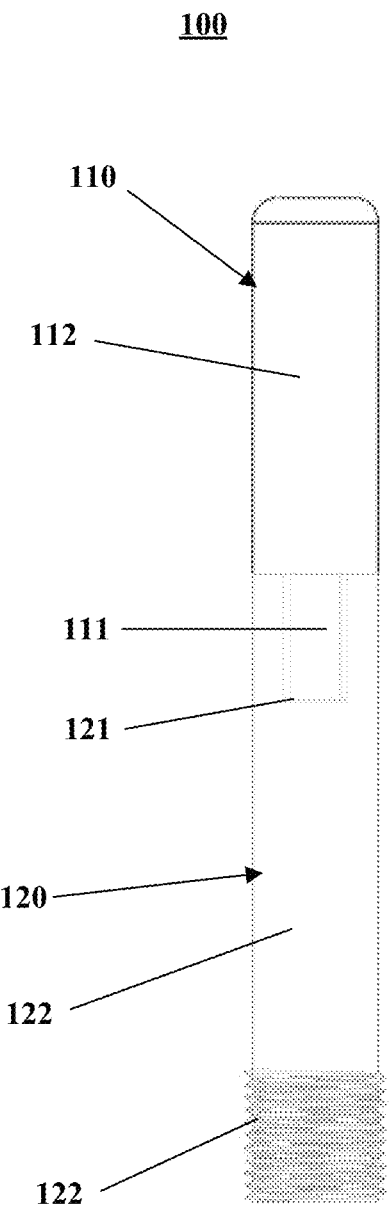
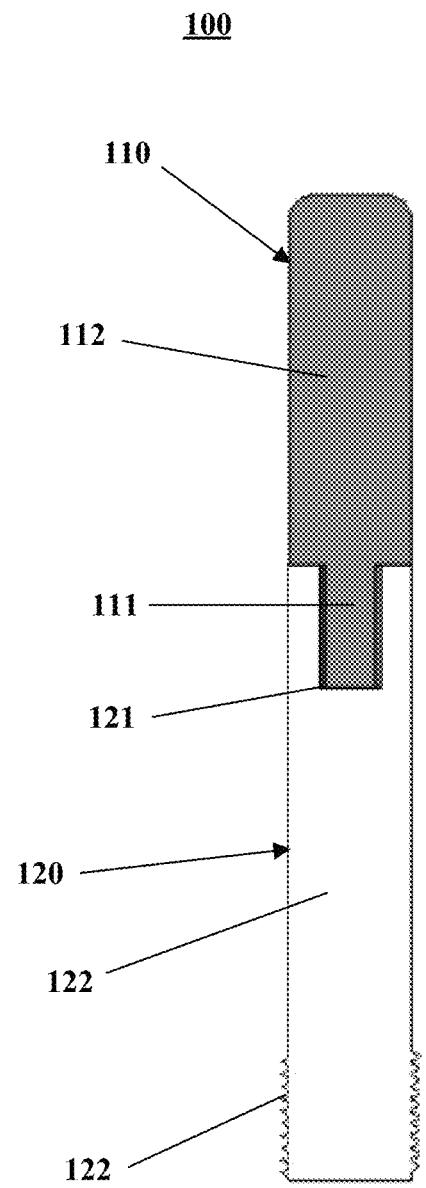
Fig. 1A
Fig. 1B

FEMORAL IMPLANT

CROSS-REFERENCE TO RELATED APPLICATIONS

The present claims priority to Application No. 62/964,330 filed Jan. 22, 2020, the disclosure of which is hereby incorporated herein by reference.

BACKGROUND

Avascular necrosis, or osteonecrosis, is the death of bone tissue when the blood supply to a portion of the bone has been interrupted or otherwise reduced. Over time, avascular necrosis results in the deterioration of bone tissue that eventually results in structural failure. Early diagnosis allows for the implementation of treatment options that can slow or stop the destruction of the diseased tissue.

One such treatment option is core decompression. Core decompression is a surgical procedure that involves drilling into necrotic bone to reduce internal pressure and increase blood flow. Avascular necrosis is frequently found in proximal femurs and can result in hip fractures particularly within the femoral head and neck. Core decompression of the proximal femur includes drilling into the femoral head and neck via a lateral side of the femur, and implanting an implant into the drilled hole. Such an implant is generally utilized to provide structural support and may have a porous structure to facilitate blood flow and bone ingrowth.

While such implants have been suitable for their intended purpose, many patients who undergo core decompression eventually have to undergo hip replacement surgery. However, hip replacement surgery may be hindered by the presence of the core decompression implant as hip replacement procedures often require the femoral head to be removed by cutting through the femoral neck. In this regard, the core decompression implant is a barrier to femoral head resection and, therefore, must be removed. Removal of core decompression implants is difficult, time consuming and can unnecessarily damage portions of the bone surrounding the implant particularly where bone has grown into its porous structure. The other option is to cut through the core decompression implant when resecting the bone. However, this may be difficult, if not impossible, as such implants are typically made from hard metals and would otherwise produce metallic debris that would almost inevitably be left behind in the patient leading to potential complications. Regardless, even where a portion of the implant is cut away along with the femoral head, the remaining portion of the implant would still require removal to make room for the joint prosthesis. Therefore, further improvements are desirable.

BRIEF SUMMARY

In accordance with an aspect of the disclosure, a method comprising cutting a channel through a femoral neck and into a femoral head of a femur, and inserting a femoral implant within the channel such that a porous portion of the femoral implant is positioned within the femoral head and a resorbable portion of the femoral implant is positioned within the femoral neck, the porous portion being coupled to the resorbable portion and extending therefrom along a longitudinal axis of the femoral implant, the resorbable portion having a cross-sectional area defined in a plane extending transverse to a longitudinal axis of the femoral implant, the cross-sectional area of the resorbable portion consisting essentially of a resorbable material. The porous portion may be inserted such that the porous portion is positioned entirely within the femoral head. The resorbable portion may be inserted such that a length of the resorbable portion is positioned within the trochanteric region of the femur. The method may further comprise securing the femoral implant to the femur by rotatably engaging a helical thread adjacent a trailing end of the resorbable portion with the femur. Securing the femoral implant may include engaging an instrument with the trailing end of the implant, and rotating the instrument to engage the set of threads with the femur. The resorbable material may be selected from one of polylactic acid, polyglycolic acid, magnesium, magnesium alloys, hydroxyapatite, and tricalcium phosphate. The porous portion may be made from one of titanium, stainless steel, cobalt-chromium, and niobium. The porous portion may comprise a porous outer surface having a porosity adapted to promote bony ingrowth.

In accordance with another aspect of the disclosure, a method comprising cutting a channel through a femoral neck and into a femoral head of a femur, and inserting a femoral implant within the channel such that a first portion of the femoral implant is positioned within the femoral head and a second portion of the femoral implant is positioned within the femoral neck, the first portion comprising a porous material adapted to promote bony ingrowth, and the second portion consisting essentially of a resorbable material. The first portion and second portion may join at an intermediate section of the femoral implant such that the first portion extends from the intermediate section to a distal end of the femoral implant and the second portion extends from the intermediate section to a proximal end of the femoral implant. The inserting step may include threadedly engaging the femur with a thread of the femoral implant. The thread may be disposed along the second portion. The inserting step may include engaging recess at the proximal end of the femoral implant with an instrument and rotating the femoral implant within the channel via the instrument. The first portion may be made from one of titanium, stainless steel, cobalt-chromium, and niobium. The resorbable portion may be made from one of polylactic acid, polyglycolic acid, magnesium, magnesium alloys, hydroxyapatite, and tricalcium phosphate. The first portion may have a projection extending partially into the second portion so as to secure the first portion to the second portion.

In accordance with yet another aspect of the disclosure, a method of preparing a femur for a joint prosthesis after a femoral implant had been implanted to treat avascular necrosis, comprising cutting through a femoral neck of a femur and an area of the femoral neck where a portion of a previously implanted femoral implant has been at least partially resorbed within the femoral neck so as to remove a femoral head of the femur and a porous portion of the femoral implant disposed within the femoral head, cutting through a trochanteric region of the femur and into an intramedullary canal thereof to form a channel for a joint prosthesis, and inserting a stem of a joint prosthesis within the channel. Cutting through the femoral neck region may include resecting a femoral head containing the porous portion of the femoral implant without contacting the porous portion. Cutting through the trochanteric region may include removing at least a portion of the femoral neck where the portion of the previously implanted femoral implant has been at least partially resorbed within the femoral neck.

In yet another aspect of the disclosure, a femoral implant comprising a porous portion configured to be received in a femoral head of a femur and having a leading end and a coupling end disposed opposite the leading end, and a resorbable portion configured to be at least partially received within a femoral neck of a femur, the resorbable portion having a trailing end and a coupling end disposed opposite the trailing end, wherein the coupling ends of the porous portion and resorbable portions are coupled together such that the leading end of the porous portion forms a leading end of the femoral implant and the trailing end of the resorbable portion forms a trailing end of the femoral implant and a longitudinal axis of the femoral implant extends through the leading and trailing ends. The resorbable portion may have at least one helical thread adjacent the trailing end. The trailing end may define an instrument recess configured to receive a driver tool. An exterior surface of the porous portion may have a porous structure adapted to promote bony ingrowth therein. The porous portion and the resorbable portion are cylindrical and may have a same outer diameter. The porous portion may include a projection the coupling end and the resorbable portion has a coupling recess at its coupling end, the projection being receivable within the recess so as to secure the porous portion to the resorbable portion. The projection may be at least one of press-fit, taper-fit, snap-fit, threaded connection, or splined connection within the coupling recess. The porous portion may have a first section and a second section, the first and second sections having different porosities. The porous portion may be made from a metallic material and the resorbable portion is made from a bioresorbable plastic.

In a yet further aspect of the disclosure, a method of treating avascular necrosis of a femur comprising in a first surgical procedure, inserting a femoral implant through a trochanteric region of the femur such that a first portion of the implant is positioned within the femoral head and a second portion of the femoral implant is positioned within a femoral neck of the femur, and in a second surgical procedure, cutting through the femoral neck and the second portion of the femoral implant so as to remove the femoral head along with the first portion of the femoral implant to prepare the bone for a hip prosthesis. The first portion comprises a porous material and the second portion may comprise a resorbable material.

BRIEF DESCRIPTION OF THE DRAWINGS

These and other features, aspects, and advantages of the present invention will become better understood with regard to the following description, and accompanying drawings.

FIG. 1A is a partial transparent front view of an implant according to one aspect of the present disclosure.

FIG. 1B is a cross-sectional view of the implant of FIG. 1 taken along a midline thereof.

DETAILED DESCRIPTION

Figure 2A:
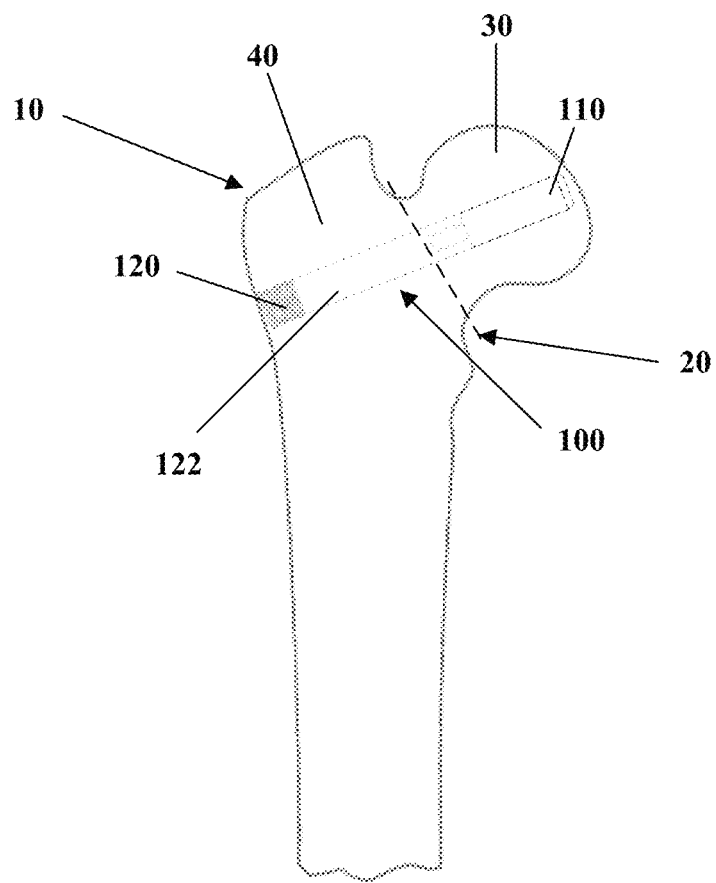
FIGS. 2A-2B depicts the method of implanting the implant of FIG. 1 and subsequently implanting a joint prosthesis according to an aspect of the present disclosure.

As used herein, when referring to the femur or other parts of the body, the term "proximal" means closer to the heart, and the term "distal" means more distant from the heart. The term "inferior" means toward the feet of a patient, and the term "superior" means towards the head of the patient. The term "anterior" means towards the front part of the body or the face, and the term "posterior" means towards the back of the body. The term "medial" means toward the midline of the body, and the term "lateral" means away from the midline of the body. When referring to an implantable device, the term "proximal" means closer to the surgeon, while the term "distal" means further from the surgeon.

FIGS. 1A-1B depicts an implant 100. Implant 100 is an osteonecrosis head pin or a core decompression implant that includes a first portion 110 and a second portion 120. First portion 110 has a substantially cylindrical body 112 and projection 111. However, in some embodiments, body 112 may be conically shaped, for example. Body 112 preferably has a porous structure that comprises at least an outer surface thereof to allow for bone in-growth therein. In this regard, body 112 may have a solid core with the porous structure surrounding the solid core. However, in some embodiments, body 112 may be entirely porous. Such porous structure provides stability of implant 100 within the patient. For example, where implant 100 is inserted within a femur, bone tissue from the femoral neck and head can grow into first portion 110 such that implant 100 is more stably held in place and prohibits back-out of such implant 100 from the bone.

In the embodiment depicted in FIGS. 1A-1B, the porosity of the porous structure of body 112 may be about 10% to 90% with an average pore size of between 20-1000 microns. However, body 112 preferably includes a pore size of between 100 and 700 microns with a mean pore size of 400 to 500 microns and a mean porosity of 55% to 65%. Examples of such a porous structure are described in U.S. Pat. Nos. 9,456,901 and 9,135,374, which are incorporated by reference herein in their entirety. In addition, body 112 can have either a uniform or varying levels of porosity throughout its porous structure. For example, body 112 can have a first internal porosity encompassed by a second surface porosity where the first porosity is greater or smaller than the second porosity. Although a distal or leading end of first portion 110 is depicted as having rounded edges, in alternative aspects, the distal end of first portion 110 can have a planar or sharp edge.

Projection 111 extends proximally from a proximal end of body 112 and is configured to be received within second portion 120. As described below, second portion and first portion may be coupled via press-fit, taper-fit, snap-fit, threaded connection, splined connection, and the like. Second portion 120 can also be over-molded onto projection 111. In this regard, in one embodiment, projection 111 may be tapered to facilitate a taper-fit connection. In another embodiment, projection 111 may be cylindrical and have an outer diameter slightly larger than a corresponding opening of second portion 120. In an even further embodiment, projection 111 may include one or more threads helically extending along the length thereof for threaded connection with second portion 120. In a yet further embodiment, projection 111 may include a plurality of splines extending outwardly therefrom for receipt in corresponding recesses in second portion 120. Projection 111 preferably has a solid structure to facilitate connection with 120 and to provide strength to such connection.

Each of solid and porous layers of first portion 110 is preferably constructed from one or more biocompatible metals, such as but not limited to any one of or any combination of titanium and its alloys, stainless steel and its alloys, magnesium and its alloys, cobalt and its alloys including a cobalt chrome alloy, nickel and its alloys, silver, tantalum, and niobium. It is also contemplated that first portion 110 may be made from one or more biocompatible polymers, such as but not limited to any one of or any combination of polyethylene (PE) and variations thereof, polyetheretherketone (PEEK), polyetherketone (PEK), acrylonitrile butadiene styrene (ABS), silicone, and cross-linked polymers.

Second portion 120 is substantially cylindrical, and includes a helical thread 122 at the proximal or trailing end and a recess or opening 121 at the distal end of the second portion 120. However, in some embodiments, second portion 120 may be conically-shaped. Thread 122 may be self-tapping or otherwise configured to engage the surrounding bone tissue when implant 100 is inserted within the patient. Recess 121 is configured and sized to receive projection 111 of first portion 110 so as to couple first and second portions 110, 120. Projection 111 can be secured within recess 121 in a variety of ways, as mentioned above. Therefore, recess 121 may configured for any one of such means. For example, where projection 111 is threadably received within recess 121, recess 121 may have corresponding internal threads. Alternatively, recess 121 may be correspondingly tapered or dimensioned for a taper-fit or press-fit connection.

Second portion 120 is preferably made of a resorbable material such that the entirety of its cross-sectional dimension constitutes a resorbable material. In other words, the entire thickness of second portion 120 is resorbable at at least one location along the length of second portion 120 so that there is no portion of the cross-sectional area at such location that is made from a contaminating debris creating material, such as metal. This allows a surgeon to cut through second portion 120 in a subsequent surgical procedure, after the resorbable material of second portion 120 is fully resorbed or at least partially resorbed, without creating potentially contaminating debris. In some arrangements, second portion 120 may be made of bioresorbable glass, ceramics, plastics, and biological active materials including collagen/cell matrices. Additional bioresorbable materials may include polylactic acid, polyglycolic acid, magnesium, magnesium alloys, hydroxyapatite, and tricalcium phosphate.

However it is contemplated that only a portion of the cross-section of second portion 120 may be made of a resorbable material while not affecting the basic and novel characteristics of implant 100. For instance, second portion 120 can define a channel that extends along at least a portion of the length of second portion 120. In this regard, a cross-section of second portion 120 may include a bioresorbable material, such as the materials mentioned above, and an empty region unoccupied by material. In an alternative aspect, it is contemplated that a core of soft biocompatible material that would not leave any debris when cut can be surrounded by an outer layer of bioresorbable material.

Moreover, in alternative aspects, second portion 120 may be substantially smooth and have no thread, or a plurality of threads. In a further alternative aspect, thread 122 can be located along any portion of the length of second portion 120 such as, for example, at an intermediate portion or distal end of the second portion. In a yet further alternative aspect, second portion 120 can include a recess (not shown) at the proximal end for receiving an instrument, such as a driver. In this manner, the instrument can rotate implant 100 to secure implant 100 to the surrounding bone tissue.

Figure 2B:
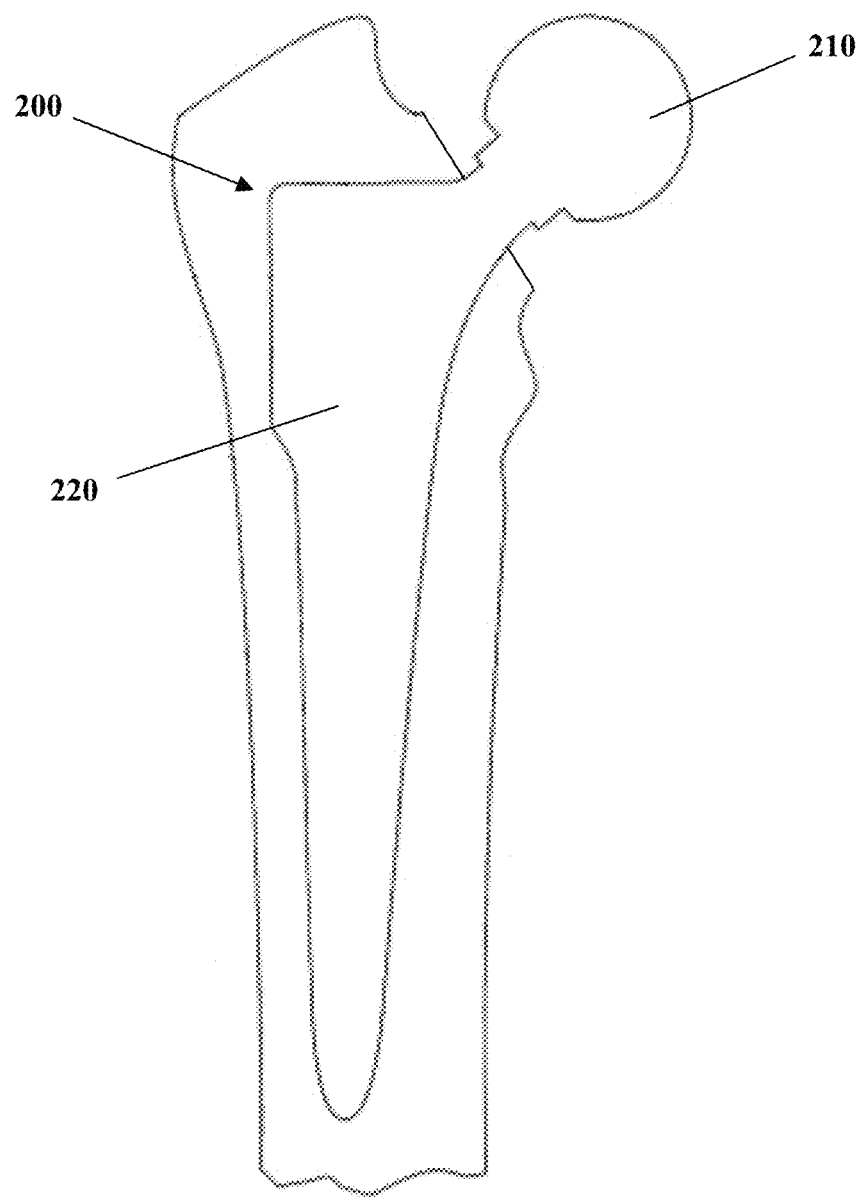

The use of implant 100 will now be described with reference to FIGS. 2A-2B. A channel (not shown) is cut (e.g., through drilling, broaching, reaming, or the like) into femur 10, through trochanteric region 40 and femoral neck 50, and into femoral head 30. Implant 100 is then inserted into the channel leading with first portion 110. Implant 100 is then secured to trochanteric region 40 through rotating second portion 120 such that thread 122 engages with the surrounding bone tissue. Over time, bone may grow into the porous structure of first portion 112 to further secure implant 100 to the bone. FIG. 2A depicts the final position of implant 100 where first portion 110 lies within femoral head 30, and a first section of second portion 120 lies within trochanteric region 40 and a second section of second portion 120 lies within femoral neck 50. Where the proximal end of implant 100 includes a recess for receiving an instrument (not shown), the instrument can rotate second portion 120 to secure implant 100 within femur 10.

Implant 100 along with the core decompression can help extend the viability of necrotic bone. However, whether through normal cartilage wear or bone deterioration, a hip replacement may be necessary. In such an instance, implant 100 allows for easy removal and implantation of the hip prosthesis.

In this regard, where second portion 120 is made of a resorbable material, as described above, the second portion 120 may have been partially or fully resorbed into the bone. Thus, only first portion 110 of the original implant 100 may remain. However, even where second portion 120 has not been fully resorbed, its resorbable nature allows it to be easily cut without concerns that leftover debris will contaminate the patient. In this case, removing implant 100 includes imaging femur 10 to locate first portion 110 within the femur. In this manner, a resection line 20 can be marked on femur 10 via a preoperative plan to cut and remove first portion 110 without cutting into the first portion. The surgeon can then cut along resection line 20 to remove and discard first portion 110 along with femoral head. Referring to FIG. 2B, the femur 10 may then be prepared as usual for the hip prosthesis 200 by forming a channel (not shown) in the proximal femur 10 for prosthesis 200. Prosthesis 200 is then inserted into the channel such that stem 220 is received in the channel and ball joint 210 protrudes for engagement with an acetabular cup (not shown).

Previous methods of removing an implant within the femur required carefully cutting the bone tissue around the implant to remove the implant to minimize the chances of accidentally cutting into the implant and leaving metal debris within the patient. As previously described, this increases the surgical complexity of dealing with avascular necrosis. Implant 100 helps treat avascular necrosis while eliminating the complexity imposed in subsequent hip replacement procedures by existing core decompression implants. In this regard, the subsequent procedure does not require a lengthy and difficult process to remove implant 100. As such, the surgeon simply resects along line 20, as shown in FIG. 2B and prepares the femur according to the surgeon's normal practice.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of preparing a femur for a joint prosthesis after a femoral implant had been previously implanted to treat avascular necrosis, comprising:

determining a resection line along a femoral neck of the femur that avoids a porous portion of the previously implanted femoral implant positioned within a femoral head of the femur, wherein a resorbable portion of the femoral implant at least partly positioned within the femoral neck of the femur has been completely resorbed or partially resorbed such that only some resorbable material remains;

cutting through the femoral neck of the femur along the resection line so as to remove the femoral head of the femur and the porous portion of the femoral implant disposed within the femoral head, wherein cutting through the femoral neck of the femur is performed without having previously removed any portion of the femoral implant from the femur;

cutting into the femur and into an intramedullary canal thereof to form a channel for a joint prosthesis; and inserting a stem of the joint prosthesis within the channel.

2. The method of claim 1, wherein cutting through the femoral neck region includes resecting a femoral head containing the porous portion of the femoral implant without contacting the porous portion.

3. The method of claim 1, cutting through the femoral neck of the femur includes removing at least a portion of the femoral neck where the portion of the previously implanted femoral implant has been at least partially resorbed within the femoral neck.

4. The method of claim 1, wherein determining the resection line is performed by imaging.

\* \* \* \* \*